US010219812B2

(12) United States Patent
Torrie et al.

(10) Patent No.: US 10,219,812 B2
(45) Date of Patent: Mar. 5, 2019

(54) DRILL GUIDE

(75) Inventors: Paul Alexander Torrie, Marblehead, MA (US); Brian J. White, Denver, CO (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

(21) Appl. No.: 13/288,867

(22) Filed: Nov. 3, 2011

(65) Prior Publication Data

US 2012/0136357 A1    May 31, 2012

Related U.S. Application Data

(60) Provisional application No. 61/409,560, filed on Nov. 3, 2010.

(51) Int. Cl.
*A61B 17/17* (2006.01)
*A61B 17/16* (2006.01)
*A61B 17/00* (2006.01)
*A61B 90/00* (2016.01)

(52) U.S. Cl.
CPC ...... *A61B 17/1746* (2013.01); *A61B 17/1739* (2013.01); *A61B 17/1778* (2016.11); *A61B 2017/0046* (2013.01); *A61B 2090/034* (2016.02)

(58) Field of Classification Search
CPC .... A61B 2017/0046; A61B 2017/1778; A61B 2019/304; A61B 17/1746; A61B 17/1714; A61B 17/1739; A61B 17/1742
USPC ......... 606/79–81, 91, 96–98, 102, 104, 86 R
See application file for complete search history.

(56) References Cited

U.S. PATENT DOCUMENTS

| 86,016 A | 1/1869 | Howell |
| 3,347,234 A | 10/1967 | Voss |
| 3,508,334 A | 4/1970 | Weissman |
| 3,604,487 A | 9/1971 | Gilbert |
| 3,867,932 A | 2/1975 | Huene |
| 4,039,266 A * | 8/1977 | O'Connell ............ 408/202 |
| 4,159,716 A | 7/1979 | Borchers |
| 4,363,250 A | 12/1982 | Suga |
| 4,580,563 A | 4/1986 | Gross |

(Continued)

FOREIGN PATENT DOCUMENTS

| CN | 1069644 A | 3/1993 |
| CN | 1625370 A | 6/2005 |

(Continued)

OTHER PUBLICATIONS

Kayvani, K. "Analysis and Design of Cable Supponed Roof Structures." <https://books.google.com/books?id=xlgyl_U1lTkC&pg=PA59&lpg=PA59&dq=high+tensile+strength+steel+characteristics+flexibility&source=bl&ots=12WZYv2_LR&sig=wdmKuugAPuSRTQjyyuqJ7AKqutl&hl=en&sa=X&ei=Ke0eVYS4G8z3sAWPvYC4CA&ved=0CE4Q6AEwBw#v=onepage&q&f=true> accessed May 14, 2015.*

(Continued)

*Primary Examiner* — Kevin T Truong
*Assistant Examiner* — Marcela I Shirsat
(74) *Attorney, Agent, or Firm* — Burns & Levinson, LLP; Joseph M. Maraia (57) ABSTRACT

The present invention relates to a drill guide for use in drilling an acetabular tunnel. The drill guide comprises a cannulated shaft having a handle towards a proximal end, and an offset arm towards a distal end. The arm is flexible or pivotable and has a distal tip for engaging the articular surface of the acetabulum, and is offset from a projected path of the shaft cannulation.

20 Claims, 6 Drawing Sheets

(56) References Cited

U.S. PATENT DOCUMENTS

| | | | |
|---|---|---|---|
| 4,708,139 A | 11/1987 | Dunbar | |
| 4,712,547 A | 12/1987 | Bonnet | |
| 4,721,116 A | 1/1988 | Schintgen | |
| 4,722,331 A | 2/1988 | Fox | |
| 4,739,751 A | 4/1988 | Sapega et al. | |
| 4,830,023 A | 5/1989 | de Toledo et al. | |
| 4,896,663 A | 1/1990 | Vandewalls | |
| 4,917,699 A | 4/1990 | Chervitz | |
| 4,960,134 A | 10/1990 | Webster | |
| 5,152,764 A | 10/1992 | Goble | |
| 5,152,790 A | 10/1992 | Rosenberg et al. | |
| 5,176,515 A | 1/1993 | Andrews | |
| 5,197,971 A | 3/1993 | Bonutti | |
| 5,207,753 A | 5/1993 | Badrinath | |
| 5,231,989 A | 8/1993 | Middleman et al. | |
| 5,250,055 A | 10/1993 | Moore et al. | |
| RE34,502 E | 1/1994 | Webster, Jr. | |
| 5,289,963 A | 3/1994 | McGarry et al. | |
| 5,292,330 A | 3/1994 | Shutt | |
| 5,320,626 A * | 6/1994 | Schmieding | 606/96 |
| 5,345,937 A | 9/1994 | Middleman et al. | |
| 5,356,064 A | 10/1994 | Green et al. | |
| 5,364,002 A | 11/1994 | Green et al. | |
| 5,366,479 A | 11/1994 | McGarry et al. | |
| 5,409,490 A | 4/1995 | Ethridge | |
| 5,458,602 A | 10/1995 | Goble et al. | |
| 5,484,095 A | 1/1996 | Green et al. | |
| 5,497,933 A | 3/1996 | DeFonzo et al. | |
| 5,514,144 A | 5/1996 | Bolton | |
| 5,520,693 A | 5/1996 | McGuire et al. | |
| 5,545,175 A | 8/1996 | Abidin et al. | |
| 5,549,617 A | 8/1996 | Green | |
| 5,562,664 A | 10/1996 | Durlacher | |
| 5,562,689 A | 10/1996 | Green et al. | |
| 5,573,538 A | 11/1996 | Laboureau | |
| 5,575,801 A | 11/1996 | Habermeyer et al. | |
| 5,584,839 A | 12/1996 | Gieringer | |
| 5,601,550 A | 2/1997 | Esser | |
| 5,609,596 A | 3/1997 | Pepper | |
| 5,613,971 A | 3/1997 | Lower et al. | |
| 5,637,112 A | 6/1997 | Moore et al. | |
| 5,643,273 A | 7/1997 | Clark | |
| 5,643,294 A | 7/1997 | Tovey et al. | |
| 5,645,549 A | 7/1997 | Boyd et al. | |
| 5,667,509 A * | 9/1997 | Westin | 606/80 |
| 5,667,513 A | 9/1997 | Torrie et al. | |
| 5,681,320 A | 10/1997 | McGuire | |
| 5,716,360 A | 2/1998 | Baldwin et al. | |
| 5,720,753 A | 2/1998 | Sander et al. | |
| 5,776,075 A | 7/1998 | Palmer | |
| 5,817,109 A | 10/1998 | McGarry et al. | |
| 5,820,630 A | 10/1998 | Lind | |
| 5,843,108 A | 12/1998 | Samuels | |
| 5,865,361 A | 2/1999 | Milliman et al. | |
| 5,885,300 A | 3/1999 | Tokuhashi et al. | |
| 5,891,150 A | 4/1999 | Chan | |
| 6,004,332 A | 12/1999 | Yoon et al. | |
| 6,022,356 A | 2/2000 | Noyes et al. | |
| 6,024,708 A | 2/2000 | Bales et al. | |
| 6,048,354 A | 4/2000 | Lawrence | |
| 6,079,606 A | 6/2000 | Milliman et al. | |
| 6,120,511 A | 9/2000 | Chan | |
| 6,123,678 A | 9/2000 | Palmer | |
| 6,129,683 A | 10/2000 | Sutton | |
| 6,136,010 A | 10/2000 | Modesitt et al. | |
| 6,200,322 B1 | 3/2001 | Branch et al. | |
| 6,210,415 B1 | 4/2001 | Bester | |
| 6,241,139 B1 | 6/2001 | Milliman et al. | |
| 6,254,605 B1 | 7/2001 | Howell | |
| 6,254,606 B1 | 7/2001 | Carney et al. | |
| 6,267,763 B1 | 7/2001 | Castro | |
| 6,330,965 B1 | 12/2001 | Milliman et al. | |
| 6,342,057 B1 | 1/2002 | Brace et al. | |
| 6,375,658 B1 | 4/2002 | Hangody et al. | |
| 6,450,948 B1 | 9/2002 | Matsuura et al. | |
| 6,491,645 B1 | 12/2002 | Gaber | |
| 6,508,496 B1 | 1/2003 | Huang | |
| 6,582,451 B1 | 6/2003 | Marucci | |
| 6,656,205 B1 | 12/2003 | Manhes | |
| 6,669,073 B2 | 12/2003 | Milliman et al. | |
| 6,701,812 B1 | 3/2004 | Sawamura | |
| 6,716,228 B2 | 4/2004 | Tal | |
| 6,840,932 B2 | 1/2005 | Lang | |
| 6,918,916 B2 | 7/2005 | Gobel et al. | |
| 6,929,647 B2 | 8/2005 | Cohen | |
| 6,953,139 B2 | 10/2005 | Milliman et al. | |
| 6,964,668 B2 | 11/2005 | Modesitt et al. | |
| 7,001,400 B1 | 2/2006 | Modesitt et al. | |
| 7,090,680 B2 | 8/2006 | Bonati et al. | |
| 7,112,208 B2 | 9/2006 | Morris et al. | |
| 7,192,431 B2 | 3/2007 | Hangody et al. | |
| 7,201,756 B2 | 4/2007 | Ross et al. | |
| 7,204,839 B2 * | 4/2007 | Dreyfuss et al. | 606/96 |
| 7,235,087 B2 | 6/2007 | Modesitt et al. | |
| 7,264,622 B2 | 9/2007 | Michelson | |
| 7,303,107 B2 | 12/2007 | Milliman et al. | |
| 7,341,564 B2 | 3/2008 | Zwiefel | |
| 7,341,596 B2 | 3/2008 | Heppler | |
| 7,351,201 B2 | 4/2008 | Ouchi | |
| 7,422,594 B2 | 9/2008 | Zander | |
| 7,481,824 B2 | 1/2009 | Boudreaux et al. | |
| 7,488,327 B2 | 2/2009 | Rathbun et al. | |
| 7,565,993 B2 | 7/2009 | Milliman et al. | |
| 7,594,917 B2 | 9/2009 | Whittaker et al. | |
| 7,624,902 B2 | 12/2009 | Marczyk et al. | |
| 7,624,903 B2 | 12/2009 | Green et al. | |
| 7,625,378 B2 | 12/2009 | Foley | |
| 7,681,772 B2 | 3/2010 | Green et al. | |
| 7,828,187 B2 | 11/2010 | Green et al. | |
| 7,842,042 B2 | 11/2010 | Reay-Young | |
| 7,871,422 B2 | 1/2011 | Shibata | |
| 7,985,239 B2 | 7/2011 | Suzuki | |
| 8,197,482 B2 | 6/2012 | Stone | |
| 8,282,647 B2 | 10/2012 | Re | |
| 8,317,862 B2 | 11/2012 | Troger et al. | |
| 8,343,161 B2 | 1/2013 | Re | |
| 8,523,872 B2 | 9/2013 | Ek | |
| 8,617,168 B2 | 12/2013 | Bourque et al. | |
| 8,685,033 B2 | 4/2014 | Johnson et al. | |
| 8,690,885 B2 | 4/2014 | Smith | |
| 8,771,273 B2 | 7/2014 | Homan et al. | |
| 8,790,352 B2 | 7/2014 | Smith et al. | |
| 8,840,615 B2 | 9/2014 | Bourque | |
| 2001/0016746 A1 | 8/2001 | McGuire et al. | |
| 2001/0053934 A1 | 12/2001 | Schmieding | |
| 2002/0019649 A1 | 2/2002 | Sikora et al. | |
| 2002/0117533 A1 | 8/2002 | Milliman et al. | |
| 2002/0117534 A1 | 8/2002 | Green et al. | |
| 2002/0133165 A1 | 9/2002 | Whittaker et al. | |
| 2002/0143342 A1 | 10/2002 | Hangody et al. | |
| 2002/0143354 A1 | 10/2002 | Lang | |
| 2003/0009173 A1 | 1/2003 | McGuire et al. | |
| 2003/0009218 A1 | 1/2003 | Boucher et al. | |
| 2003/0083688 A1 | 5/2003 | Simonson | |
| 2003/0083695 A1 | 5/2003 | Morris | |
| 2003/0093093 A1 | 5/2003 | Modessitti et al. | |
| 2003/0216742 A1 | 11/2003 | Wetzler et al. | |
| 2004/0015170 A1 | 1/2004 | Tallarida et al. | |
| 2004/0049195 A1 | 3/2004 | Singhatat et al. | |
| 2004/0073227 A1 | 4/2004 | Dreyfuss et al. | |
| 2004/0147932 A1 | 7/2004 | Burkinshaw et al. | |
| 2004/0181246 A1 | 9/2004 | Heppler | |
| 2004/0193172 A1 | 9/2004 | Ross et al. | |
| 2004/0220588 A1 | 11/2004 | Kermode et al. | |
| 2004/0267276 A1 | 12/2004 | Camino et al. | |
| 2005/0027299 A1 | 2/2005 | Metzger | |
| 2005/0033365 A1 | 2/2005 | Courage | |
| 2005/0113841 A1 | 5/2005 | Sheldon | |
| 2005/0149045 A1 | 7/2005 | Elliott | |
| 2005/0165420 A1 | 7/2005 | Cha | |
| 2005/0177179 A1 | 8/2005 | Baynham et al. | |
| 2005/0222601 A1 | 10/2005 | Erhard | |
| 2005/0228399 A1 | 10/2005 | Kubo et al. | |
| 2005/0245924 A1 | 11/2005 | Tuke et al. | |

(56) References Cited

U.S. PATENT DOCUMENTS

| | | |
|---|---|---|
| 2005/0245934 A1 | 11/2005 | Tuke |
| 2005/0261692 A1 | 11/2005 | Carrison et al. |
| 2006/0041263 A1 | 2/2006 | Chu et al. |
| 2006/0069394 A1 | 3/2006 | Weiler et al. |
| 2006/0085006 A1 | 4/2006 | Ek et al. |
| 2006/0106398 A1 | 5/2006 | Lauryssan et al. |
| 2006/0119014 A1 | 6/2006 | Towers et al. |
| 2006/0155290 A1 | 7/2006 | Shino |
| 2006/0195106 A1* | 8/2006 | Jones et al. ............ 606/79 |
| 2006/0195112 A1 | 8/2006 | Ek |
| 2006/0271059 A1 | 11/2006 | Reay-Young |
| 2007/0118136 A1 | 5/2007 | Ek |
| 2007/0152014 A1 | 7/2007 | Gillujm et al. |
| 2007/0179340 A1 | 8/2007 | Jorgenson |
| 2007/0191852 A1 | 8/2007 | Shimko et al. |
| 2007/0191853 A1 | 8/2007 | Stone |
| 2007/0233128 A1 | 10/2007 | Schmieding et al. |
| 2007/0233136 A1 | 10/2007 | Wozencroft |
| 2007/0233151 A1 | 10/2007 | Chudik |
| 2007/0233241 A1 | 10/2007 | Graf et al. |
| 2007/0244508 A1 | 10/2007 | Weizman |
| 2007/0270804 A1 | 11/2007 | Chudik |
| 2007/0276370 A1 | 11/2007 | Altarac et al. |
| 2007/0282356 A1 | 12/2007 | Remiszewski et al. |
| 2007/0282358 A1 | 12/2007 | Remiszewski et al. |
| 2008/0027435 A1 | 1/2008 | Zucherman et al. |
| 2008/0027457 A1 | 1/2008 | Dienst et al. |
| 2008/0097453 A1 | 4/2008 | Stone |
| 2008/0103506 A1 | 5/2008 | Volpi et al. |
| 2008/0140748 A1 | 6/2008 | Lada |
| 2008/0188859 A1 | 8/2008 | Reitzig et al. |
| 2008/0221581 A1 | 9/2008 | Shoham |
| 2008/0306485 A1 | 12/2008 | Coon et al. |
| 2008/0306487 A1 | 12/2008 | Hart |
| 2009/0018654 A1 | 1/2009 | Schmieding et al. |
| 2009/0048673 A1 | 2/2009 | Le Huec |
| 2009/0069845 A1 | 3/2009 | Frushell et al. |
| 2009/0076512 A1 | 3/2009 | Ammann et al. |
| 2009/0143784 A1 | 6/2009 | Petersen et al. |
| 2009/0157081 A1 | 6/2009 | Homan et al. |
| 2009/0157110 A1 | 6/2009 | Muto et al. |
| 2009/0163766 A1 | 6/2009 | Torrie |
| 2009/0163935 A1 | 6/2009 | McCarthy et al. |
| 2009/0171355 A1 | 7/2009 | Amis et al. |
| 2009/0171360 A1 | 7/2009 | Whelan |
| 2009/0216236 A1 | 8/2009 | Re |
| 2009/0216243 A1 | 8/2009 | Re |
| 2009/0222013 A1 | 9/2009 | Graf et al. |
| 2009/0228031 A1 | 9/2009 | Ritter et al. |
| 2009/0254093 A1 | 10/2009 | White |
| 2009/0281545 A1* | 11/2009 | Stubbs ............ 606/87 |
| 2009/0306675 A1 | 12/2009 | Wong et al. |
| 2010/0016984 A1 | 1/2010 | Trabish |
| 2010/0030029 A1 | 2/2010 | Markham |
| 2010/0030116 A1 | 2/2010 | Chana |
| 2010/0042106 A1 | 2/2010 | Bryant et al. |
| 2010/0049200 A1* | 2/2010 | Re ............ A61B 17/1714 606/89 |
| 2010/0049201 A1 | 2/2010 | Re |
| 2010/0057077 A1 | 3/2010 | Ducharme |
| 2010/0068233 A1 | 3/2010 | Bangera et al. |
| 2010/0121337 A1 | 5/2010 | Pandya |
| 2010/0137872 A1 | 6/2010 | Kam et al. |
| 2010/0137924 A1 | 6/2010 | Tuke |
| 2010/0249930 A1 | 9/2010 | Myers |
| 2010/0256645 A1 | 10/2010 | Zajac et al. |
| 2010/0268241 A1 | 10/2010 | Flom et al. |
| 2010/0292743 A1 | 11/2010 | Singhal |
| 2011/0087258 A1 | 4/2011 | Sluss |
| 2011/0251621 A1* | 10/2011 | Sluss ............ A61B 17/1742 606/96 |
| 2011/0282350 A1 | 11/2011 | Kowarsch et al. |
| 2011/0313478 A1 | 12/2011 | Herdrich et al. |
| 2012/0046526 A1* | 2/2012 | Boettner ............ A61B 17/0218 600/210 |
| 2012/0059382 A1 | 3/2012 | Paulos |
| 2012/0059469 A1 | 3/2012 | Myers et al. |
| 2012/0109136 A1 | 5/2012 | Bourque et al. |
| 2012/0116402 A1 | 5/2012 | Schneider |
| 2012/0150301 A1 | 6/2012 | Gamache et al. |
| 2012/0197261 A1 | 8/2012 | Rocci et al. |
| 2013/0085494 A1 | 4/2013 | Weisenburgh et al. |
| 2014/0107657 A1 | 4/2014 | Norton et al. |
| 2014/0303635 A1 | 10/2014 | Smith et al. |

FOREIGN PATENT DOCUMENTS

| | | |
|---|---|---|
| CN | 201182625 Y | 1/2009 |
| CN | 201612662 U | 10/2010 |
| DE | 102007057075 A1 | 5/2009 |
| EP | 0643945 A2 | 3/1995 |
| EP | 1444959 A1 | 8/2004 |
| EP | 1882456 A | 1/2008 |
| EP | 1917921 A2 | 5/2008 |
| EP | 2311394 A1 | 4/2011 |
| FR | 2716364 A | 8/1995 |
| FR | 2906452 A1 | 4/2008 |
| FR | 2911264 A1 | 7/2008 |
| FR | 2918554 A1 | 1/2009 |
| GB | 2230453 A | 10/1990 |
| JP | H10-174689 | 6/1998 |
| JP | 2002102236 A | 4/2002 |
| JP | 2003531676 | 10/2003 |
| JP | 2005507697 A | 3/2005 |
| JP | 2009195705 A | 9/2009 |
| JP | 2009261812 | 11/2009 |
| JP | 2010527705 | 8/2010 |
| JP | 2011507639 A | 3/2011 |
| JP | 2011520475 A | 7/2011 |
| JP | 201275604 | 4/2012 |
| RU | 2125844 C1 | 2/1999 |
| RU | 2241394 C2 | 12/2004 |
| RU | 46642 U1 | 7/2005 |
| WO | 8800458 A1 | 1/1988 |
| WO | 9929237 A1 | 6/1999 |
| WO | 9956628 | 11/1999 |
| WO | 0140748 A1 | 6/2001 |
| WO | 2001/82838 A2 | 11/2001 |
| WO | 0236020 A1 | 5/2002 |
| WO | 2003037163 A2 | 5/2003 |
| WO | 2005037065 A2 | 4/2005 |
| WO | 2005037150 A1 | 4/2005 |
| WO | 2006088452 A2 | 8/2006 |
| WO | 2009082497 A1 | 7/2009 |
| WO | 2012103535 A1 | 8/2012 |
| WO | 2014107729 A2 | 7/2014 |

OTHER PUBLICATIONS

International search report and written opinion regarding International patent application PCT/US2011/059216 dated Feb. 14, 2012.
International search report and written opinion regarding International patent application PCT/US2011/059219 dated Feb. 10, 2012.
International Preliminary Report on Patentability from corresponding International application No. PCT/US2011/059216 dated May 16, 2013.
Communication pursuant to Article 94(3) for EP11781969.8 dated May 27, 2015.
Office Action from related European Application No. 11781969.8-1654 dated May 23, 2016.
Kayvani, K., "Analysis and Esign of Cable Supported Roof Structures," <https://books.google.com/books?id=xlgyI_U1lTkC&pg=PA59&lpg=PA59&dq=high+tensile+strangth+steel+characteristics+flexibility&source=bl&ots=l2WZYv2_LR&sig=wdmKuugAPuSRTQjyvuqJ7AKqutl&hl=en&sa=X&ei=Ke0eVYS4G8z3sAWPvYC4CA&ved=0CE4Q6AEwBw#v=onepage&q&f=true> accessed May 14, 2015.
Matsuda, D.K.,"FAI: An emerging problem in orthopedics," Orthopedics Today, Jul. 2009, Retrieved from www.healio.com on Jan. 11, 2013.

(56) References Cited

OTHER PUBLICATIONS

Shino, Konsei, "Triple Bundle ACL Reconstruction Using the Smith and Nephew ENDOBUTTON CL Fixation System" Knee Series. Technique Guide. Andover, Massachusetts: 2007.
Office Action from related Mexican Application No. MX/a/2013/003496 dated Jun. 6, 2017.
Communication from related EP Application No. 08729966.5-1659 dated Jul. 7, 2017.
Notice of Reasons for Rejection from related Japanese Application No. 2013-557915 (Appeal No. 2016-12398) dated Jul. 14, 2017.

* cited by examiner

DRILL GUIDE

The present invention relates to a drill guide. In particular, the present invention relates to a drill guide for use in hip arthroscopy.

In many joints, when the bones forming the joint are operated at the extremes in their range of motion, damage can occur through trauma and also interference between the bones. In the hip, for example, when the femur is flexed upwards it may collide with the rim of the socket or acetabulum, of the pelvis. When this occurs, any soft tissue which is caught between the colliding bones may be damaged and cause pain to the individual. The soft tissue that is caught in this manner is usually the labrum, which is a ring-like structure formed from cartilage that surrounds the acetabular rim.

The labrum improves stability of the hip joint by effectively deepening the hip socket to provide extra structural support to the joint. It also helps to create a negative intra-articular pressure which partially seals the joint and acts to prevent it from being distracted. In addition, the cartilage tissue of the labrum acts as a buffer between adjacent bone surfaces of the hip joint and provides an articular surface which permits the joint to move fluidly. This helps to prevent wear and tear on the joint by stopping the bones of the joint from directly grinding against one another.

The acetabular labrum has an irregular shape and comprises essentially three parts. The first connects the labrum to the acetabular rim. The second is an extension of the articular surface of the acetabulum, and provides an internal articular surface, and the third is an external surface where the hip joint capsule attaches.

Cartilage tissue only has a very limited capacity for repair as it does not contain any blood vessels, and so where damage has occurred the growth of new tissue is extremely slow, if at all.

Due to advances in arthroscopic surgical procedures on the hip, the number of labral tears being identified has markedly increased. Such tears can be caused by injury through a specific trauma or repetitive movements, or by degeneration. Femoral acetabular impingement, interference caused by naturally occurring irregularities on the generally spherical head of the femur with the rim of the acetabulum, can also lead to such tears. Often, an individual will be completely unaware of a tear in their labrum and will not display any symptoms. Such cases will not generally require treatment. However, in more severe cases an affected individual may experience pain and stiffness, or limited range of motion in their hip joint or groin. They may also notice a locking, clicking or catching sensation in the affected hip.

Arthroscopic repair of a torn hip labrum can be approached in several ways, depending on the severity of the tear. The damaged tissue may be removed by debridement to relieve pain for flap tears. Where the tear is more severe, bioabsorbable suture can be utilised to hold the tear together whilst the cartilage tissue heals. This is generally only successful in regions where there is a good blood supply. Where the damage is severe and the labrum has become detached from the acetabular rim, reattachment is often necessary and this typically requires the use of one or more bone anchors.

In surgical repairs where suture anchors are required in the reattachment of a torn labrum back to the bony rim of the acetabulum, it is necessary to drill bone tunnels within the acetabulum. Due to the inherent anatomy of the hip, and the restriction on the arthroscopic trajectories which are available to a surgeon, the procedure for drilling bone tunnels to accommodate the suture anchors is challenging. Placement and pitch of the tunnels relative to the acetabular rim is critical in order to avoid a 'blow-out' of the acetabular cartilage, or the back of the acetabulum itself Previously, this issue has typically been dealt with in one of two ways. The surgeon may force a drill guide into what is deemed to be the correct trajectory by using brute force, and then visually determine whether the projected drill path would cause the a blow-out of the acetabulum or acetabular cartilage.

Alternatively, a curved drill guide can be used to enable standard portals and trajectories to be used. Using a curved guide allows the drill to bend and enter the acetabulum at an angle which minimises any potential blow-out.

However, during surgery and in the aqueous environment of the joint space, both of these approaches suffer from lens distortion with the wide angled arthroscope necessary for performing hip arthroscopy, and the high angle (70°) of the direction of view to the camera axis. Operating under these conditions, it is extremely difficult to mentally project a straight drill path through the bone with any accuracy.

A more convenient arthroscopic approach could have considerable advantages over open surgical procedures if these obstacles were overcome. In particular, it would help to reduce the number of instances acetabular blow-out. Accordingly, there exists a need for a better arthroscopic approach.

The present invention seeks to address at least some of these problems by providing a drill guide which allows bone tunnels to be drilled in the acetabulum, whilst reducing the risk of a blow-out of the acetabulum or acetabular cartilage occurring.

In its broadest sense the present invention provides a drill guide having a flexible or pivotable offset arm.

According to the present invention there is provided a drill guide for use in drilling an acetabular tunnel, comprising a cannulated shaft having a handle towards a proximal end, and an offset arm towards a distal end, wherein the arm is flexible or pivotable and comprises a distal tip for engaging the articular surface of the acetabulum, and which is offset from a projected path of the shaft cannulation.

Suitably, the arm is resiliently flexible. Suitably, the arm is formed from a Nitinol wire or plate, a Nitinol tube, or a plastics material.

Alternatively, the arm is rigid and is pivotally connected at or near the distal end of the shaft. Suitably, the pivotal connection is a hinge. Suitably, the pivotal connection a living hinge. Preferably, the pivotal connection includes biasing means. Suitably, the biasing means is a spring. All of these arrangements allow the arm to bend, flex or pivot within a single plane if a surgeon chooses a trajectory other than the default provided by the natural state of the arm.

Preferably, the drill guide includes an obturator for supporting and protecting the offset arm whilst the instrument is packaged and/or when the instrument is being introduced into a surgical site. Suitably, the obturator is a curved or flattened member, or a hollow tubular member. Preferably, the obturator is a tubular member, or at least partially tubular, coaxially mounted with the shaft. Suitably, the obturator includes an opening at a distal end. Preferably, the obturator is slidably or rotatably mounted within the shaft and interlocks with the offset arm such that it may be held substantially rigidly.

Alternatively, the obturator is an outer sheath, mounted on the outer surface of the shaft. Preferably, the outer sheath at least partly surrounds a portion of the outer surface of the shaft. Suitably, the outer sheath is slidably mounted or rotatably mounted on the shaft, or is removable. In embodiments in which the outer sheath is rotatably mounted on the shaft, the rotatable movement arises from a thread and complementary groove arrangement—for example the outer surface of the shaft may include a helical thread.

Preferably, the drill guide includes a lock. The lock helps locking the obturator when it is engaged with the offset arm and in a position for transit. The lock may be any suitable locking means, such as a twist-lock, button or catch.

Preferably, the distal end of shaft includes bone engaging means. Suitably, the bone engaging means are one or more teeth or spikes which, in use, act to prevent the distal end of the shaft from slipping when engaged with a bone surface.

Preferably, the proximal end of the shaft, or handle, includes a depth stop to prevent over-drilling of the bone tunnels. This feature helps to prevent over-drilling of the bone tunnels, by ensuring that the bone tunnels are only drilled to a depth required for the particular anchor which is being used. Suitably, the depth stop is adjustable. An adjustable depth stop allows anchors of different sizes to be used in conjunction with the drill guide—the depth stop being set according to the particular anchor size being used in the procedure.

Preferably, the offset arm includes one or more marks to define a preferred region of contact of the offset arm with the acetabular surface, during use of the instrument. Suitably, the one or more marks are at or towards the distal end of the offset arm. The mark or markings assist the surgeon in the correct usage of the instrument.

Suitably, the offset arm includes one or more bends. Bends may advantageously be incorporated into the offset arm so that only a preferred region of the arm comes into contact with tissue during use of the instrument. Alternatively, the arm may be curved, or be straight and include one or more hinges. This helps to minimise the extent of contact of the instrument with the labral tissue, to prevent damage to the tissue.

Another general aspect of the invention features a method for positioning a bone tunnel in the acetabulum using the guide discussed above. In use, the bone engaging means at the distal end of the instrument shaft are located against a surface of the acetabular rim, and the pitch of the instrument relative to the acetabulum is adjusted, and thus the trajectory of the guide, until the offset arm comes into contact with the acetabular surface. Next, a drill bit is inserted through the drill guide and the bone drilled to a depth stop. A suture anchor is then delivered down the guide and into the previously drilled bone hole. The guide is subsequently removed from the patient. Among other advantages, the invention provides an efficient and accurate way of positioning a bone tunnel, and helps to prevent a blow-out of the acetabulum or acetabular cartilage.

The current invention provides an arthroscopic instrument that uses the curved surface of the acetabular socket to guide a drill for placement of anchor tunnels in procedure for reattaching the labrum to the acetabulum. The instrument provides an offset position which allows a safe drill trajectory to be chosen before drilling takes place.

The above and other aspects of the invention will now be described with reference to the following drawings in which.

Figure 1:
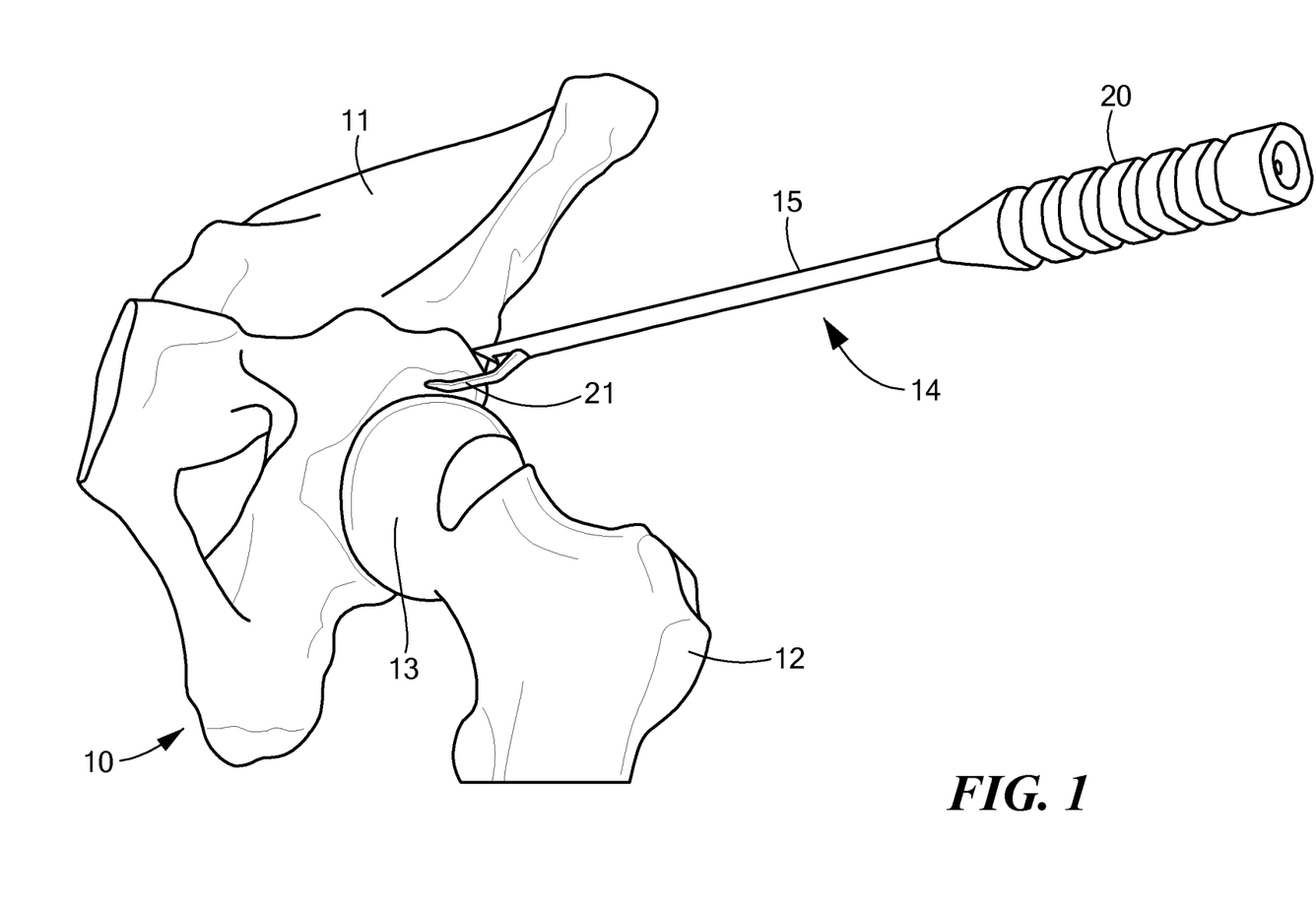
FIG. 1 is a partial view of a distracted hip joint including a first embodiment of an instrument according to the invention.

Referring to FIG. 1, there is shown a partially distracted hip, or acetabulofemoral joint 10, formed from the femur 12 and acetabulum of the pelvis 11. Femur 12 includes a substantially spherical head 13, which locates in the cup-like acetabulum of the pelvis 11. The joint is lubricated with synovial fluid and its surfaces are lined with cartilage to cushion movement and allow it to move freely (not shown). The acetabulum is lined with the acetabular labrum, which is a ring-shaped fibrocartilaginous lip. The labrum extends beyond the acetabulum, forming a tight sliding connection with the femoral head and providing a stable joint. Also shown is a drill guide 14 for assisting a surgeon when conducting drilling procedures of the acetabulum.

The drill guide comprises a shaft 15, having a handle 20 towards a proximal end, and an offset arm 21 towards a distal end. The shaft 15 is cannulated to allow the passage of a drill (not shown) during a drilling procedure. The drill guide assists a surgeon in judging where to drill the acetabulum and helps to keep the drill piece steady during the drilling process.

Figure 2:
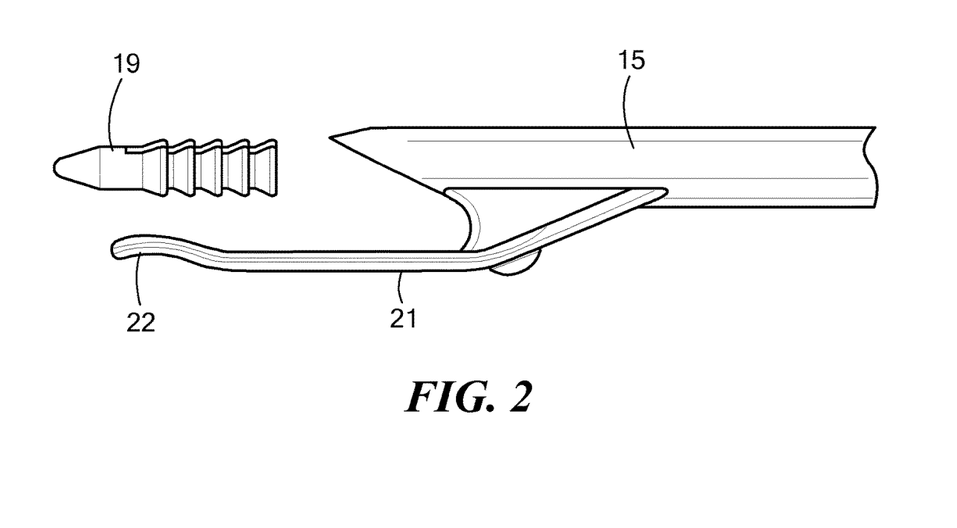
FIG. 2 is a side-view of the distal end of the instrument of FIG. 1.
Figure 3:
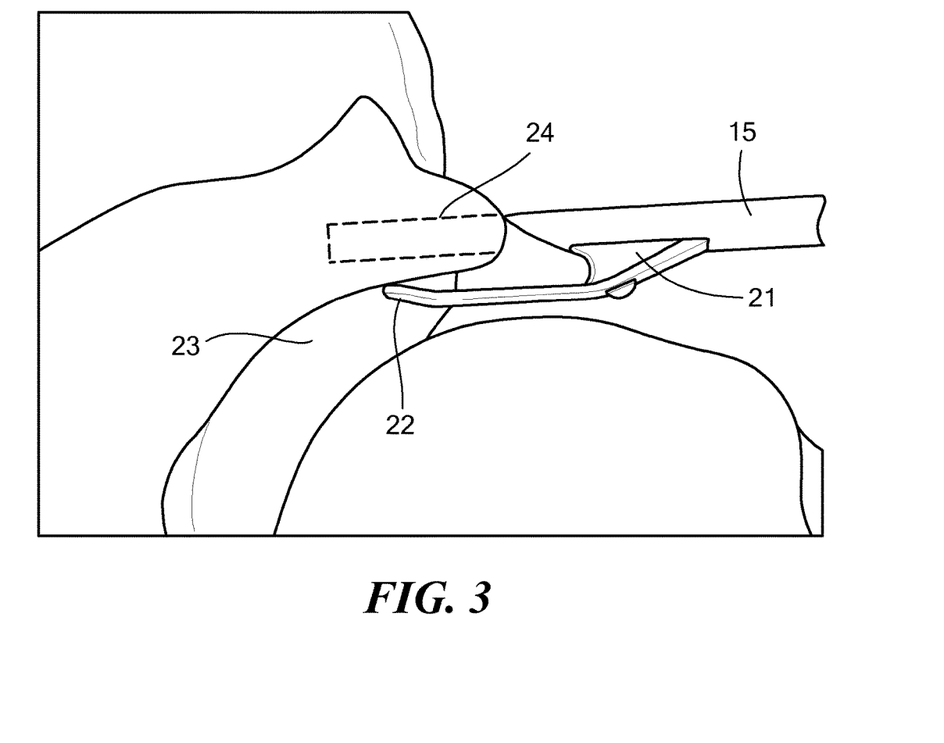
FIG. 3 is a close-up side-view of the distal end of the instrument of FIG. 1, with the hip joint shown in a partial sectional view.

As shown in FIGS. 2 and 3, the offset arm 21 helps to maintain a minimum wall thickness of bone between a bone tunnel and the articular surface of the acetabular cartilage 23, when the arm 21 remains in contact with the acetabulum during the drilling process. In the preferred embodiment of FIG. 2, the distal end or tip 22 of the offset arm 21 is shorter in length than the tunnel to be drilled. According to this illustration, the position of the anchor 19 is intended to depict its final position once it has been inserted within the drilled tunnel, and relative to the positioning of the drill guide. In alternative embodiments (not shown), the distal end or tip of the offset arm is intended to roughly correlate with the bottom of the tunnel to be drilled. To this end, a depth stop (not shown) for preventing over-drilling of the bone tunnel is provided. The depth stop may be any suitable means and can be a shoulder within the cannulated shaft or a similar such feature at the point of entry of the drill piece to the cannulated shaft, to serve the purpose of preventing over-advancement of the drill piece. Accordingly, the risk of a drill passing directly through the acetabulum and out the medial side is reduced.

The offset arm can be designed with any offset desired, and to some extent will be determined by the anatomy of a particular patient, with a larger offset resulting in a thicker the bone wall between tunnel and acetabular cartilage.

In FIG. 3, with the tip 22 of the offset arm 21 held against the acetabular cartilage 23, a bone tunnel 24 resulting from drilling using the guide is shown with hashed lines. As can be seen, the drill guide provides for a minimal bone thickness between the tunnel and acetabular cartilage 23, helping to prevent a blow-out of the acetabular cartilage.

Figure 4:
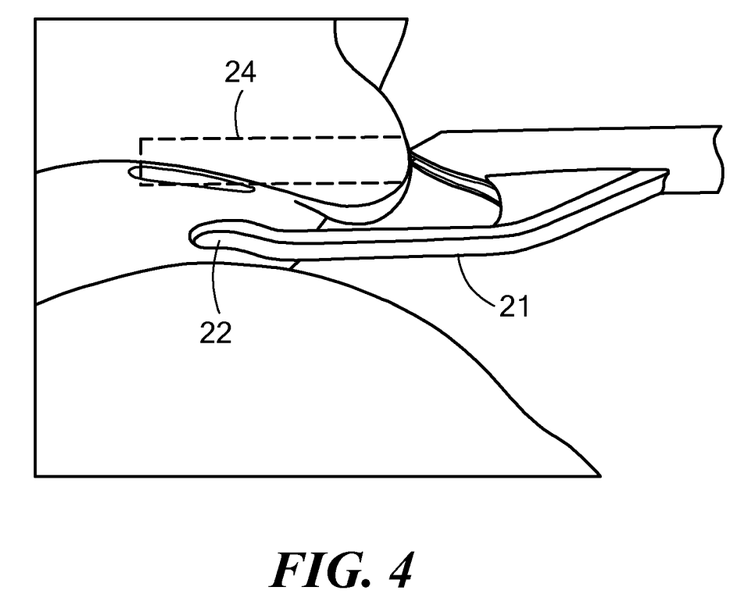
FIG. 4 is a close-up side-view of the distal end of the instrument of FIG. 1, in which a blow-out has occurred.

If the drill guide is not correctly aligned, and the tip 22 of the offset arm 21 is not abutted against the surface of the acetabular cartilage 23 of the acetabular socket during drilling, or lifts away, as shown in FIG. 4, the thickness of bone between the subsequently drilled hole and the socket or cartilage will be reduced, and a blow-out of the acetabulum may occur.

Figure 5:
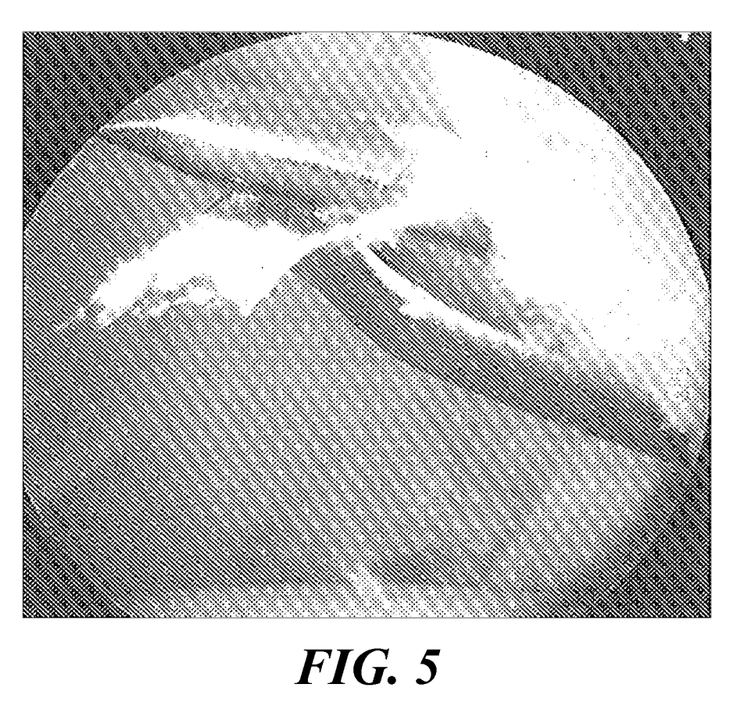
FIG. 5 is a surgical view illustrating a blow-out of the acetabulum.

An actual blow-out of the acetabular cartilage is shown in FIG. 5, where the distal tip of the offset-arm is not in contact with the articular surface of the acetabular cartilage. As a result, the drill has passed through the bone and cartilage of the acetabulum and into the joint space of the socket.

A key feature of the offset arm is that it is designed to pivot, flex or bend if the surgeon chooses a trajectory other than the minimum indicated by the arm.

Figure 6A:
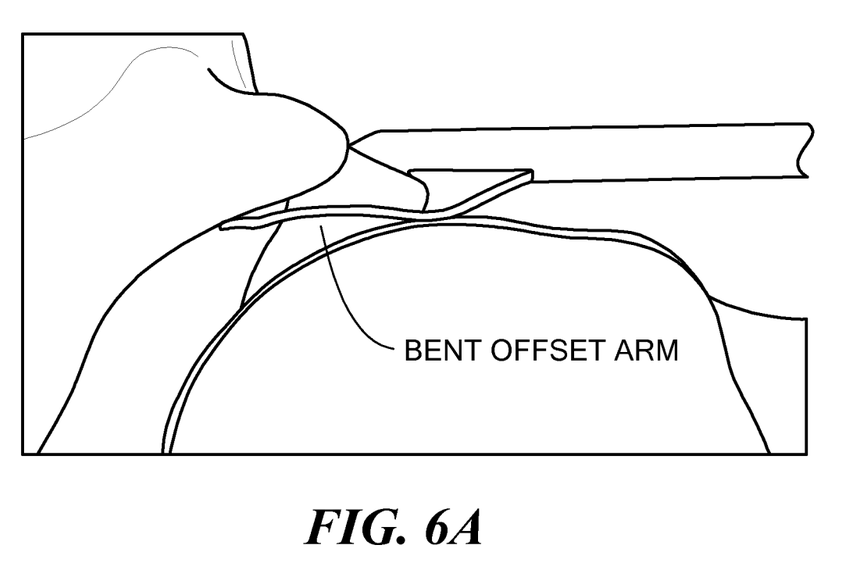
FIGS. 6A & B are, respectively, side views of the embodiment of FIG. 1 in which the offset arm is flexible and bent; and rigid and hinged.

Typically in this condition, the offset arm is curved or bent, as depicted in FIG. 6A. The arm is also resiliently flexible, and preferably formed from a material having memory properties, such as Nitinol or a suitable plastics material. In the illustrated embodiment, the offset arm is made of Nitinol that allows it to be bent yet return to its original position once the force is removed. The Nitinol arm can be screwed, pinned, riveted or welded to the cannulated shaft.

Figure 6B:
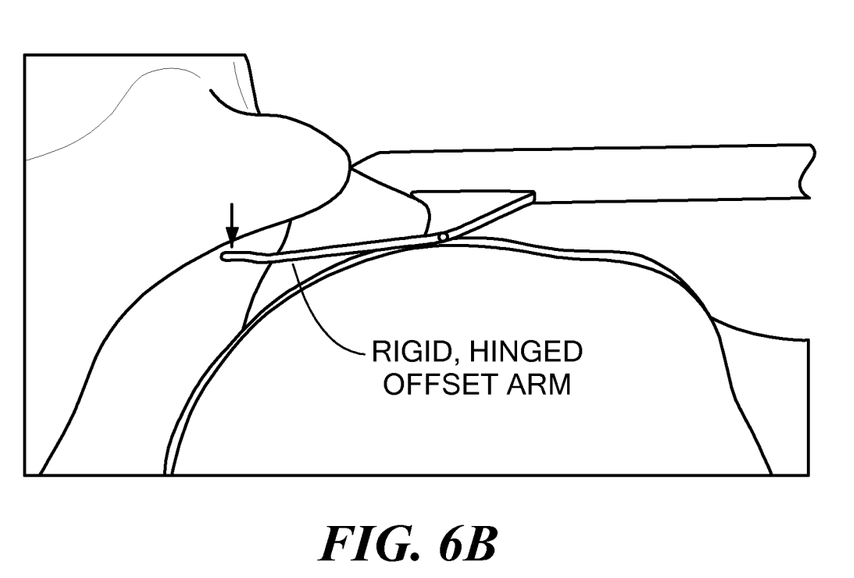

Alternatively, as shown in FIG. 6B, the offset arm may be rigid and include a pivot 'A' in a region where offset arm connects or couples with the shaft of the drill guide. The pivot can be a hinge. In such embodiments, the drill guide may include a biasing means (not shown), for example a spring, to bias the offset arm in a minimal bone thickness indicating position. The provision of a pivot permits the arm to bend only within a single plane. This is advantageous if a surgeon chooses a trajectory other than the minimum provided by the arm.

Figure 7:
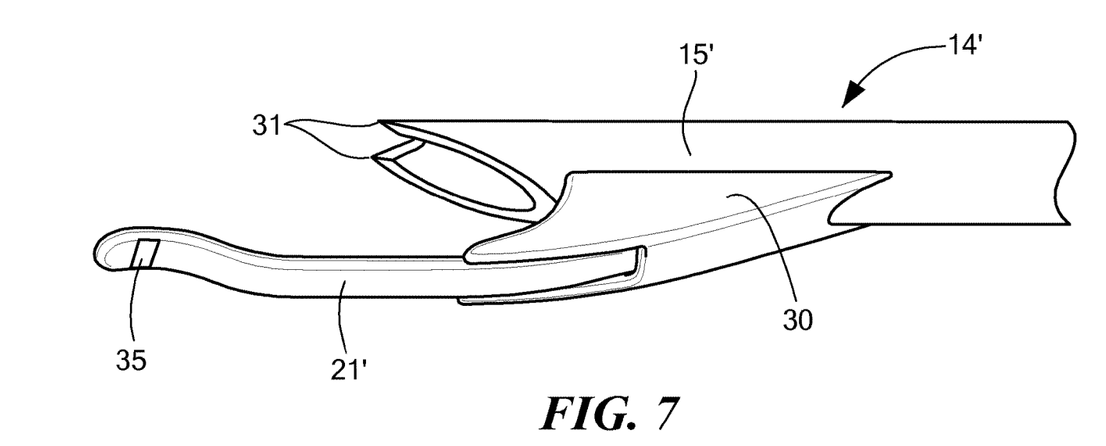
FIG. 7 is a perspective view from the side and below of the distal end of an alternative embodiment, in which the offset arm has an alternative mounting arrangement.
Figure 8:
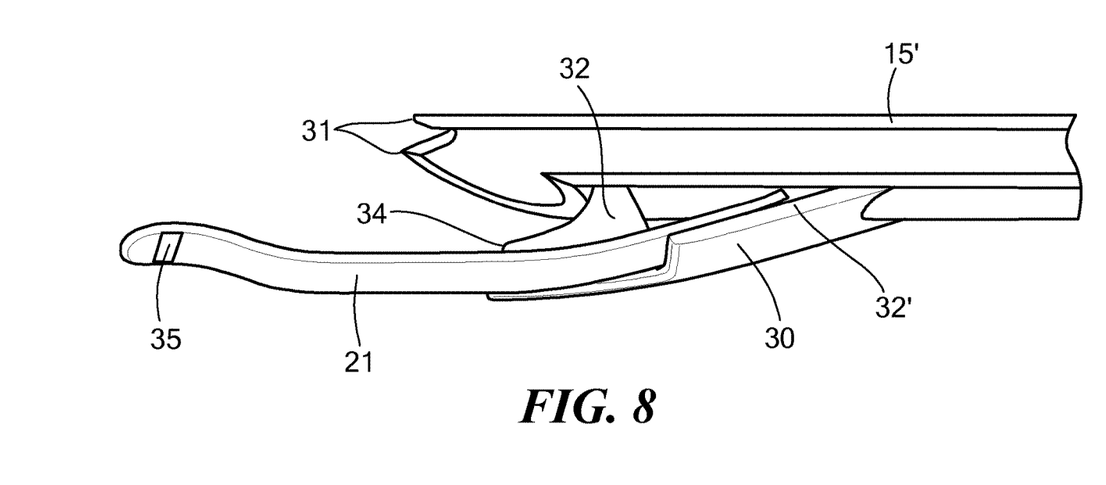
FIG. 8 is a sectional view of the embodiment of FIG. 7.
Figure 9:
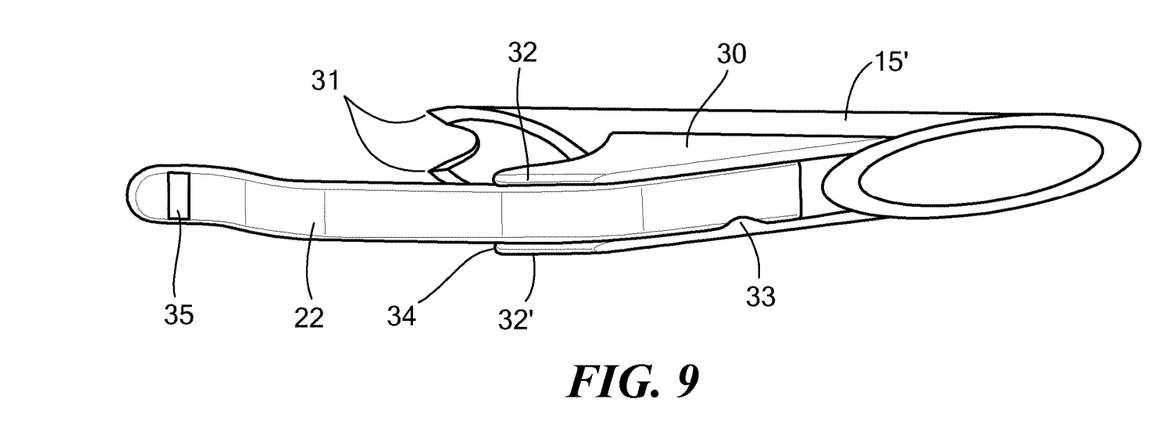
FIG. 9 is a partial sectional view, from below, of the embodiment of FIG. 7.

It is known to be difficult to weld Nitinol directly to stainless steel. In the embodiments of FIGS. 1 to 4, a Nitinol offset arm is attached to the cannulated shaft of the drill guide by means of a screw or pin. However, stress concentrations at the point of attachment, and the precision required in fixing the arm to the shaft mean that it can be difficult to manufacture drill guides in this manner. FIGS. 7 to 9 illustrate an alternative means of attaching the Nitinol arm to the cannulated shaft. In this alternative embodiment, the drill guide has a Nitinol offset arm which is formed with and trapped within a stainless steel cap. According to this construction, the stainless steel cap is welded to the cannulated shaft, which itself is preferably also formed from stainless steel. The offset arm is cantilevered relative to the shaft and steel cap. As a result, some of the difficulties of manufacture may be alleviated.

FIG. 7 shows the distal end of a drill guide 14' having an offset arm 21' formed from a resiliently flexible Nitinol finger and cap 30. In this embodiment the cap is formed from stainless steel and is welded to the cannulated shaft 15', which is also formed from stainless steel. In alternative embodiments, the cap is formed from other suitable materials.

Additionally, the distal end of cannulated shaft 15' features bone engaging means 31 to help prevent slippage of the guide once it has been placed for, and during, drilling.

Figure 10:
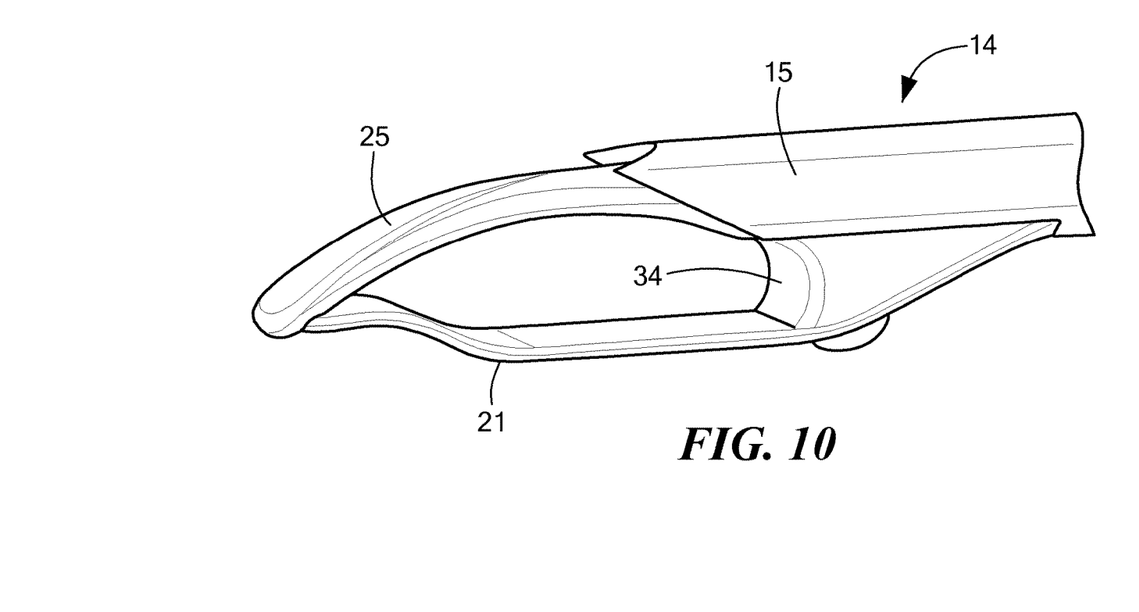
FIG. 10 is a perspective view from the side and above of the distal, end of the instrument of FIG. 1 which includes an internal obturator.

As is more clearly shown in FIGS. 8 to 10, cap 30 includes various supports 32, 32' and lip 34 for fixing the Nitinol finger within a channel of the cap, and preventing it from moving. In addition, one or more 'bumps' or projections 33 are provided on cap 30 to prevent the Nitinol finger from translating out of channel.

The distal region of the offset arm 21 also includes one or more marks 35 which define a preferred region of contact for the offset arm with the acetabular surface. The mark or marks help the surgeon to correctly position the drill guide and assist it usage of the instrument.

An obturator may also be used with the drill guide to protect the offset arm. This prevents tissue catching on the offset arm, particularly during the introduction of the drill guide into the body and joint region, and can stabilize the offset arm during insertion.

In the embodiment shown in FIG. 10, drill guide 14 includes an obturator 25 which projects from the distal end of shaft 15. The obturator may be a generally tubular member coaxially mounted with the shaft which supports and protects the offset arm 21 whilst the instrument is packaged and/or when the instrument is being introduced into a surgical site. In the embodiment shown, the obturator is retractable and moveable between a deployed position, in which the offset arm is engaged for storage or insertion into a surgical site, and a retracted position In which the obturator is housed within the shaft of the drill guide. In such embodiments, the drill guide is formed of an inner tube and an outer tube. The inner tube provides the channel through which a drill may be guided, and the region between the inner and outer tubes houses the obturator. In alternative embodiments, not shown, the obturator may simply be removed once the instrument has been inserted into the surgical site.

The obturator may be slidably or rotatably attached to the instrument, or may be removable.

In alternative embodiments, not shown, the obturator is a sheath mounted on the outer surface of the shaft of the drill guide. The sheath includes an opening at a distal end and can be moved in an axial direction for deployment or retraction. The outer sheath may be advanced and retracted by means of complementary axial threads on the outer surface of the shaft and inner surface of outer sheath. Alternatively, the outer sheath may be slid up and down the shaft, or may include a combination of both—for example, it may be advanced and retracted in a sliding manner that incorporates a twisting or screwing action at or towards the extreme ends of its desired motion in order to lock the sheath in position.

The surgical instrument may also include a lock (not shown) for locking the instrument in the stowed position for storage or passage into, or out of, the body. The lock may be any suitable locking means, such as a twist-lock, button or catch.

The drill guide also includes a depth stop (not shown). The depth-stop can be set, by suitable means, to a depth required to safely deploy a bone anchor, and acts to prevent a drill from being inserted too deeply, which would result in over-drilling of the acetabulum. For example, the depth stop may be an internal shoulder in the cannulated shaft of the drill guide or a portion of the handle. The depth stop may also be adjustable to account for bone anchors of differing sizes, or alternatively, to allow a surgeon to drill shallower/deeper bone tunnels where deemed appropriate.

The described drill guide provides an advantage over standard known straight guides because a safe drill trajectory may be chosen before drilling of an anchor hole, and also because, the estimation of a safe trajectory is eliminated. Further, it provides an advantage over existing curved guides since it eliminates any unseen trajectory changes within the joint which are sometimes difficult to comprehend when viewed through an endoscope, for the reasons mentioned previously.

The invention claimed is:

1. A drill guide for use in drilling a tunnel in bone, comprising:
   a cannulated shaft having a lumen, proximal and distal ends, and a first axis defining a projected path of the lumen, the shaft being open at its distal end;
   bone-engaging means defining one or more points of engagement at the distal end of the shaft for engaging a bone surface at the one or more points of engagement;
   a handle towards the proximal end of the shaft, and
   an offset arm formed separately from and attached to a first surface of the shaft towards the distal end of the shaft,
   wherein the offset arm is resiliently flexible and extends distally beyond the distal end of the shaft, the offset arm comprising:
      a proximal region spaced apart from the shaft having a second axis parallel to and offset from the first axis;
      a non-spherical distal tip having a blunt surface that faces and is adapted to be brought into contact with a tissue surface via a curve or bend in the offset arm toward the first axis such that the blunt surface is located between and offset from the first axis and the second axis; and
      a distal region extending between the proximal region and the distal tip;
   wherein the resilience of the offset arm is sufficient to enable a pitch of the shaft relative to the bone to be increased while maintaining the distal tip of the offset arm biased into contact with the tissue surface.

2. A drill guide according to claim 1, wherein the drill guide includes an obturator having a distal end adapted to extend beyond the distal end of the shaft and engage the offset arm at a location exteriorally of and beyond the distal end of the shaft to protect the offset arm prior to its use, the obturator being removable when the device is to be used.

3. A drill guide according to claim 2, wherein the obturator is a curved or flattened member, or a hollow tubular member.

4. A drill guide according to claim 3, wherein the obturator is a tubular member, or at least partially tubular, coaxially mounted within the shaft.

5. A drill guide according to claim 2, wherein the obturator is slidably or rotatably mounted within the shaft and interlocks with the offset arm so as to enable maintaining the offset arm in a rigid position.

6. A drill guide according to claim 1 wherein the bone engaging means comprises a plurality of teeth or spikes extending from a second surface of the shaft which, in use, act to prevent the distal end of the shaft from slipping when engaged with the bone surface, the second surface of the shaft being opposite the first surface of the shaft.

7. A drill guide according to claim 1, wherein the proximal end of the shaft, or handle, comprises an adjustable depth stop to prevent over-drilling of the bone tunnels.

8. A drill guide according to claim 1, wherein the offset arm is configured to flex only in a single plane.

9. A drill guide according to claim 1, wherein a minimum acceptable drilling trajectory relative to the bone is predefined and wherein the drill guide is configured so that the drill guide is angled at and aligned with the minimum acceptable trajectory when the bone engaging means at the distal end of the drill guide are positioned against the bone surface.

10. A drill guide according to claim 9, wherein the offset arm is configured to define a range of acceptable trajectories for the drill guide.

11. A drill guide according to claim 1, wherein the distal portion of the offset arm is bent such that only the blunt surface of the distal tip of the offset arm comes into contact with the tissue surface.

12. A drill guide according to claim 11, wherein the offset arm includes one or more marks to define the preferred region for contacting the tissue surface.

13. A drill guide according to claim 1, wherein the shaft comprises a first material and the offset arm comprises a second material selected to be more resiliently flexible than the first material.

14. A drill guide according to claim 13, wherein the second material is Nitinol or a plastics material.

15. A method for positioning and drilling a bone tunnel in bone, comprising the steps of:
    locating a bone engaging means at a distal end of a drill guide against a bone surface, the drill guide comprising:
      a cannulated shaft having a lumen, proximal and distal ends, and an axis defining a projected path of the lumen, the shaft being open at its distal end; the bone-engaging means defining one or more points of engagement at the distal end of the shaft for engaging the bone surface at the one or more points of engagement;
      a handle towards the proximal end of the shaft, and
      an offset arm formed separately from and attached to a first surface of the shaft towards the distal end of the shaft, wherein the offset arm is resiliently flexible and extends distally beyond the distal end of the shaft, the offset arm comprising:
         a proximal region spaced apart from the shaft having a second axis parallel to and offset from the first axis;
         a non-spherical distal tip having a blunt surface that faces and is adapted to be brought into contact with a tissue surface via a curve or bend in the offset arm toward the first axis such that the blunt surface is located between and offset from the first axis and the second axis; and
         a distal region extending between the proximal region and the distal tip;
      wherein the resilience of the offset arm is sufficient to enable a pitch of the shaft relative to the bone to be increased while maintaining the distal tip of the offset arm biased into contact with the tissue surface;
    positioning the drill guide relative to the bone so that the offset arm is in contact with the tissue surface;
    inserting a drill bit into the drill guide; and
    while maintaining the offset arm in contact with the tissue surface, drilling into the bone to a desirable depth.

16. The method as defined in claim 15 further comprising delivering a suture anchor into the drilled hole, and removing the drill guide, leaving the suture anchor in place.

17. The method as defined in claim 15 further comprising the step of, while the offset arm is in contact with the tissue surface, increasing the pitch of the shaft against the resilience of the offset arm.

18. The method as defined in claim 15 wherein the steps are performed arthroscopically.

19. The method as defined in claim 15, further comprising pivoting the drill guide relative to the bone about a pivot so as to bias the offset arm against the tissue surface thereby causing the offset arm to flex.

20. The method as defined in claim 15, wherein a minimum acceptable drilling trajectory relative to the bone is predefined and wherein the drill guide is configured so that the drill guide is angled at and aligned with the minimum acceptable trajectory when the bone engaging means at the distal end of the drill guide are positioned against the bone surface.

\* \* \* \* \*